[19] United States Patent
DiFoggio

[11] Patent Number: 4,920,792
[45] Date of Patent: May 1, 1990

[54] METHOD FOR DETERMINING THE AMOUNT OF FLUID IN A CORE

[75] Inventor: Rocco DiFoggio, Houston, Tex.

[73] Assignee: Shell Oil Company, Houston, Tex.

[21] Appl. No.: 164,153

[22] Filed: Mar. 4, 1988

[51] Int. Cl.$^5$ ............................................. F21B 49/00
[52] U.S. Cl. ...................................... 73/153; 208/188;
   208/348; 436/31
[58] Field of Search ...................... 73/38, 153; 203/14;
   208/188, 348; 422/69, 280, 281, 292; 436/31,
   143

[56] References Cited
U.S. PATENT DOCUMENTS
3,200,065  8/1965  Cottington ......................... 208/348
4,265,860  5/1981  Jennings et al. ..................... 422/280

Primary Examiner—Hezron E. Williams
Assistant Examiner—Kevin D. O'Shea

[57] ABSTRACT

Methods and apparatus are provided to extract oil and brine fluids from a representative porous sample. The petrophysical properties of these extracted oil and brine fluids may be determined by conventional or other testing methods. The oil fluids and brine fluids are separated from each other by separate distillation and condensation, and by removing the solvent from the oil fluids. The amounts of oil and brine fluids from the sample may then be separately determined. The apparatus uses a desiccant container at the top of a soxhlet tower beneath the cold finger (which condenses the solvent gases that have been evaporated) in a pressure soxhlet extractor to capture any brine or water and thus, separate the brine or water from the oil and/or solvent which remain in the soxhlet extraction chamber at the bottom of the soxhlet tower.

9 Claims, 1 Drawing Sheet

METHOD FOR DETERMINING THE AMOUNT OF FLUID IN A CORE

BACKGROUND OF THE INVENTION

The present invention relates to the exploration and production of petroleum from earth formations, and more particularly, to methods for determining the amount of fluids present in such a formation.

In the petroleum industry, one of the most valuable and informative techniques for determining the characteristics of an earth formation located well below the surface, and the nature of the fluids which it may contain, is to remove and bring a portion of the formation and/or its fluids to the surface for analysis. This is done most commonly by "coring" the formation. This coring may be accomplished by conventional coring, pressure coring or sponge coring, when it is desired to recover a substantial portion of a formation or formations. However, sidewall plugs or cores are also employed, when only a small portion of the earth formation is desired or when more economical samples are desired.

It is often important to type the hydrocarbon crude in order to be able to determine the ease of removal of the crude oil. A reliable method for estimating key hydrocarbon properties, such as API gravity, from sidewall samples could preclude the need for expensive production testing. The potential economics through reduced costs and/or reduced risks to a well could be substantial. Further, variations in hydrocarbon properties within or between reservoirs could be more easily determined with increased sample density at lower cost.

The importance of coring in the production of petroleum has recently been increasing as more and more secondary and tertiary recovery is being made of petroleum reserves. In a formation undergoing primary production, the original reservoir fluids are little altered from their condition for the last several thousand or more years. They may migrate as the oil is produced, but their properties are not changed significantly. However, when fluids and/or other compounds are injected into a formation to stimulate its production, the nature of the connate fluids is accordingly altered, sometimes to a very substantial extent. When this occurs, the more traditional well-logging tools may be unable to provide any useful information about the formation and/or its fluids. In all too many instances, the only way to determine how much oil is left, and thus whether it can be produced economically, is to physically recover a portion of the formation by taking a core sample.

It will therefore be appreciated that the analysis of the amount and properties (viscosity, API gravity, etc.) of the oil in a core sample can be critically important. The viscosity (which is correlated to API gravity) of the crude in a formation often determines whether the oil in the formation may be commercially produced. Similarly, the final true residual oil saturation of a formation is a determination that can make or break a multi-million dollar enhanced recovery project.

Typically, oil is extracted from a portion of a core by means of a soxhlet extractor. Other techniques are also available such as the Dean Stark extraction technique. However, typically these prior art techniques use a hot solvent which dissolves the oil and boils off the water that is found in the core sample. This is usually the result of using a solvent that is capable of dissolving only the oil and not the water. At the end of the extraction, the oil recovered remains in the solvent and is usually discarded. The soxhlet technique only cleans the sample. In Dean-Stark analysis, the condenser is placed to the side of the extraction vessel's center line and any water that is boiled off is condensed and collected in a side arm under the condenser; the (generally lighter) solvent then floats on top of the collected water and overflows the sidearm to drip back onto the sample. In Dean-Stark analysis the volume of oil is inferred by subtracting the amount of water boiled out of the rock from the total pore volume of the rock. If there was any gas in the original core, the calculated oil volume will be too high.

That is, the prior art techniques can not extract and separately recover both the pure oil (essentially solvent free) and pure brine or water. Without an essentially solvent-free crude extract, it is difficult to make direct measurements of the extract properties. Further, these techniques are unable to predict produced crude properties from a crude extract that may have been adulterated due the coring and/or extraction process.

These and other limitations and disadvantages are overcome by the present invention, however, and methods and apparatus are provided for determining the amount of fluids in a core sample, and the petrophysical properties of those fluids.

SUMMARY OF THE INVENTION

In a preferred embodiment of the present invention, methods and apparatus are provided for determining the amount of fluids in a core sample and determining the petrophysical properties of those respective fluids.

The apparatus of the present invention is a modified pressure soxhlet extractor that employs a special solvent. In particular, the special solvent is one that is capable of dissolving both the oil and brine (or water) simultaneously and has a very low boiling point (i.e. is a liquified gas at room temperature). The soxhlet extractor is modified to include a small container for special desiccant at the top of the soxhlet tower beneath the cold finger (which condenses the solvent gases that have been evaporated). The modified apparatus uses the desiccant container to capture any brine or water and thus, separate the brine or water from the oil and/or solvent which remain in the soxhlet extraction chamber at the bottom of the soxhlet tower. The brine or water may be evaporated from the desiccant and recondensed to provide an aqueous fluid for determining the petrophysical properties of such a fluid. The solvent may be removed by evaporation from the soxhlet extraction chamber leaving a small specimen of extracted crude oil in the extraction chamber. The extract may then be characterized by conventional or other testing to determine its petrophysical properties; for example, preferably the gravity of the extract is determined by near infrared techniques.

The presently preferred methods of the present invention employ a special solvent to extract fluids from a representative porous sample in a pressurized soxhlet extractor. The oil fluids and the brine fluids are separated from each other by separate distillation and condensation, and by removing the solvent from the oil fluids. The amounts of oil and brine fluids from the core may then be separately determined. From these samples of brine and oil the petrophysical properties of these fluids may be determined by conventional or other means. Preferably, the API gravity of any hydrocarbons extracted from the core specimen is determined by near infrared spectroscopy.

Further, the methods of the present invention may be employed to determine the API gravity of the actual produced crude from hydrocarbons extracted from a core specimen (which may have missing light ends) by near infrared spectroscopy. Near infrared spectroscopy is attractive because it can be used to quantify the number of C—H bonds. For example, with a special solvent, there is no remaining solvent and thus no C—H bonds from the solvent, so the oil concentration may be readily determined. Further, for near infrared spectroscopy all the properties for which a regression analysis have been developed may be determined from the same infrared spectra of a sample. Also, this near infrared method may be employed to determine the properties of either the hydrocarbon extract or the produced crude itself. Similarly, super-critical fluid chromatography determines only the aromatics, which are not present because all the solvent taught in the present invention is removed from the hydrocarbon extract by evaporation.

Additionally, a method of the present invention employs these special solvents to remove water from a crude oil, without substantially altering the properties of the the crude oil, so that the petrophysical properties of the substantially dewatered crude may then be determined.

It therefore an object of the present invention to provide methods and apparatus for determining the amounts of fluids in a core sample, and determining the petrophysical properties of those fluids.

These and other objects and advantages of the present invention will become apparent from the following detailed description, wherein reference is made to figures in the accompanying drawings.

DETAILED DESCRIPTION

Figure 1:
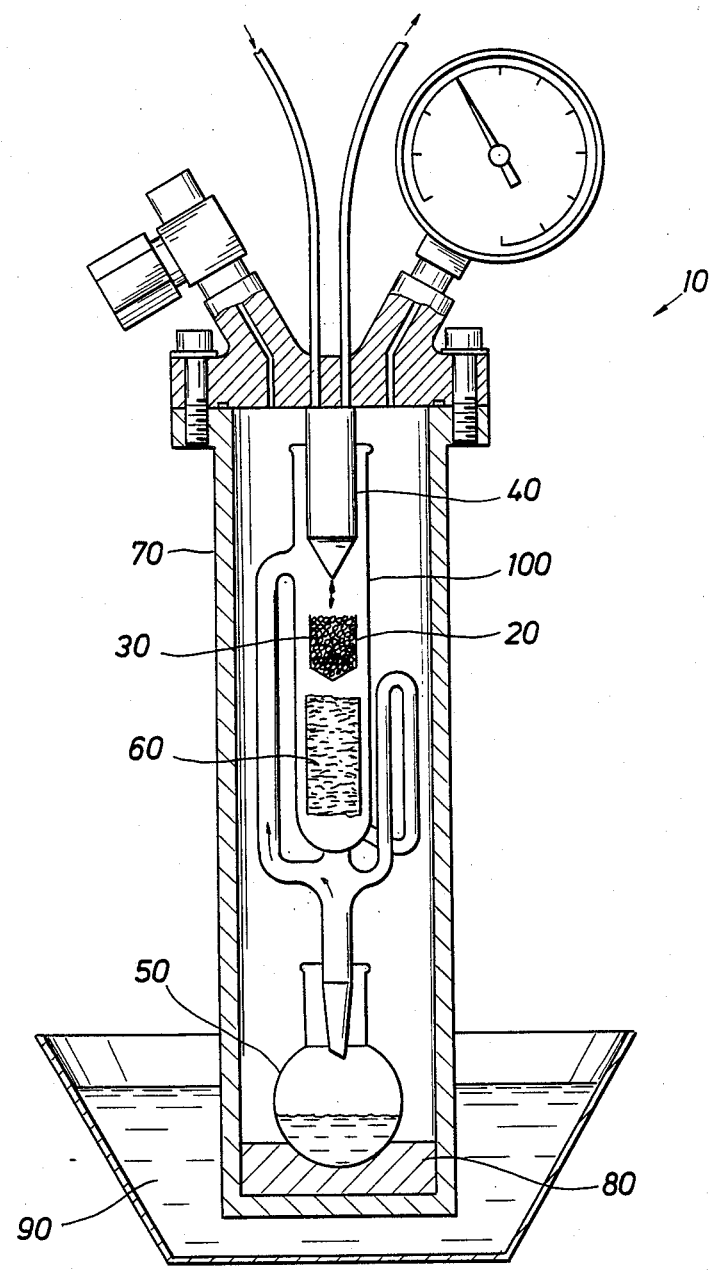
FIG. 1 is a partial cross-sectional view of a pressurized soxhlet extractor modified in accordance with the teachings of the present invention.

Referring now to FIG. 1, there may be seen a partially cross-sectional view of a pressurized soxhlet extractor assembly 10 that has been modified in accordance with the teachings of the present invention. More particularly, there may be seen to be a container 20 for desiccant 30 at the top of the soxhlet column 100 disposed immediately beneath the condenser 40 on the upper section of the soxhlet extractor assembly 10. In particular, the solvent and water vapors are rising from the sample collection and boiling flask 50 that collects any liquified solvent and extracted fluids at the base of the soxhlet tower assembly; such vapors are condensed by the condenser 40 on the upper portion of the assembly and the condensed vapors drip through this special container 20 and desiccant 30 to trap any condensed aqueous fluid. The special container 20 contains an appropriate desiccant 30 which is preferably three angstrom (3Å) molecular sieve material in pellet form. This desiccant in the special container traps any aqueous fluid i.e. forms a water trap, while allowing the liquified solvent to pass therethrough.

Further, it may be seen that the glass soxhlet extractor tower contains at its bottom portion a representative specimen of a porous sample 60. Such a porous sample may be a core sample, sponge core, or drilling cuttings. Preferably this sample is a sidewall core plug. This sample is then subjected to the extraction and cleansing action of a solvent in the conventional soxhlet extraction sense. The hydrocarbon and aqueous fluids in the porous specimen are dissolved by the special solvent and are accordingly carried by the solvent to the boiling flask 50 at the bottom of the soxhlet assembly. The special solvent is soluble in both hydrocarbon and aqueous fluids so that any hydrocarbon (oil) trapped in open pore volumes by water, or vice versa is still removed, i.e. extracted, by the special solvent.

The soxhlet tower and boiling flask are contained in a pressure vessel 70 and the boiling flask rests on a heat transfer plate 80. The bottom portion of the pressure vessel is located in a water bath 90 which may be heated, if necessary, by a heating means (not shown).

By employing a special solvent as described hereinafter, it is possible for the solvent to evaporate in the boiling flask 50 and carry any aqueous fluid (water or brine) with it, such that both the water and the solvent are recondensed by the condenser 40 at the top of the assembly. There the aqueous fluid and liquid solvent drip through the water trap and any aqueous fluids are removed by the desiccant. In this manner, the amount of aqueous fluid that was contained in the porous sample may be determined by measuring the weight of the desiccant before and after extraction. The absorbed aqueous fluid may also be evaporated from the desiccant by heat and the resulting vapors then recondensed to provide an aqueous fluid sample for determining its petrophysical properties. Once the volume of the amount of aqueous fluids is determined from its weight and density, the saturation of the aqueous fluids may be determined. The pore volume of the porous sample may be determined by the well known weighing in toluene method. Also, a lower bound on the pore volume of the sample may be determined by adding the total volumes of all the extracted fluids.

Although the water of any brine in the sample may evaporate from the boiling flask 50 along with the special solvent, any salts dissolved in the brine will also be concentrated in the boiling flask along with the extracted hydrocarbons or left as a light powder or crust on the exterior surface of the sample. The extracted hydrocarbons and salt in the boiling flask 50 may be weighed upon completion of the extraction process by weighing the boiling flask 50 containing these materials and subtracting the weight of the empty boiling flask 50. The hydrocarbons may then be removed by adding solvent that will dissolve the hydrocarbon but not the salt to allow for removal of the hydrocarbon and then reweighing of the boiling flask to determine the weight of the salt alone. The hydrocarbon weight must be reduced by this salt weight. It is then possible to knock or scrape the salt from the core sample's outer surface into the boiling flask and then obtain a better estimate of the amount (weight) of salt in the brine extracted from the sample. These salts may then be analyzed to determine their content.

As in conventional soxhlet extraction techniques the extracted hydrocarbon fluids and the solvent will collect in the bottom boiling flask 50 at the bottom of the soxhlet assembly. It is then possible to remove the solvent by evaporation or boiling which is accomplished by careful depressurization of the pressurized assembly at room temperature to leave only the extracted hydrocarbons. The weight of the hydrocarbons in the boiling flask may then be determined from the original weight of the empty boiling flask and the weight of the boiling flask containing the extracted hydrocarbons. The density of a portion of this extract may then be determined by conventional means (Mettler-Paar densitometer) to allow for a determination of the volume of the extracted hydrocarbons (oil) from the previously determined weight and density of the extracted hydrocarbons. Again, once the volume of the extracted hydrocarbons is known, the saturation of the hydrocarbons may be determined, based upon a known or measured pore volume of the porous sample.

This small sample of extracted hydrocarbon fluids from the porous specimen may then be subjected to analysis for its petrophysical properties. In particular, it is contemplated by the methods of the present invention, to conduct near infrared spectroscopy on this small extract sample to determine the API gravity and other petrophysical properties thereby. It has been found for example, that near infrared spectroscopy may determine the API gravities from a sample as small as twelve microliters. Thus, near infrared measurements are readily applicable to the extraction and characterization of hydrocarbon fluids, such as oil, from porous samples as small as sidewall plugs or a collection of drilling cuttings.

Further, near infrared measurements may be employed to determine the petrophysical properties of a produced crude from the near infrared measurements made of the extract, or the petrophysical properties of the extract itself may be determined. More particularly, the near infrared measurements may be employed to determine the API gravity of a produced crude from the near infrared measurements made of the extract. This is in spite of the fact that the extract may have lost the light ends found in the produced crude due to the coring and/or extraction process. Further, near infrared measurements may be employed to determine the API gravity of the actually extracted hydrocarbon fluids, even though the API gravity of the extract and produced crude may not and need not be the same. Other properties such as asphaltene content, aromatics, saturates, acid numbers, etc. may also be determined from near-infrared measurements.

As noted hereinabove, the solvent used to extract the water and oil fluids from the core specimen is a special solvent. In particular, such a solvent is preferably a solvent which forms an azeotrope with water, although such a solvent may co-distill with water. The criteria for these special solvents are that the solvent (1) have a low boiling point, (2) be soluble in both a hydrocarbon and aqueous fluid, (3) be safe for handling, i.e. have manageable to no toxicity and be non-flammable, (4) have a low chemical reactivity with the crudes and/or brines, and optionally, (5) be capable of dissolving salts. In particular, the solvent should be a good crude oil solvent having a minimum of asphaltene precipitation. It should be noted that these criteria for the special solvent may be mutually contradictory, so that any special solvent that is selected may not optimally satisfy all of these criteria.

Further, since conventional solvent technology indicates like-solvents dissolve like-materials, this indicates that it should be extremely difficult to find solvents which are capable of dissolving both aqueous fluids and hydrocarbon fluids, which is the most important of these criteria, along with non-reactivity with the aqueous and/or hydrocarbon fluids. The criteria of having a low boiling point even further restricts any potential solvents. Additionally if the option to dissolve salts is considered, the ability to dissolve salts restricts even more any potential solvents. In particular, for a salt dissolving solvent it is desired to have a plurality of hydrogen bonds to achieve good salt dissolution; however, the increase of hydrogen bonds normally increases the boiling point.

In general, such special solvents may be selected from cycloalkanols, cycloalkenes, cycloalkanes, alkene oxides, methyl amines, and certain freons. Specific examples of such solvents are ethylene, cyclopropane, nitrous oxide, diethyl ether, ethyl chloride, propylene, acetylene, and allene. Such solvents may have polar groups, OH groups, or more unsaturated type bonds to help dissolve asphaltenes. Alkynes have been found to have better water solubility than aromatics.

It has been found that the temperature differential between the boiling point of the crude desired to be extracted and the solvent should be on the order of 30° C. or more. Thus, for extremely heavy crudes the boiling point of the solvent is preferably in the $-10°$ C. or less boiling point range. However, higher boiling point solvents may be used with heavy crudes if the extract is subsequently heated above room temperature in a distillation apparatus to remove any residual liquified solvent.

Further, low boiling point solvents are particularly useful for extracting core samples containing gypsum, since the heating process for conventional solvents destroys the gypsum. It has been found that cyclopropane is such a low boiling point special solvent capable of extracting crude oils for "typing", as well as dewatering heavy crude oils.

It is believed at the present time that cyclopropane forms an azeotrope with water. Other special solvents are presently believed to be freon R152A and vinyl chloride. It is also contemplated by the present invention to mix various combinations of the above noted solvents to extract aqueous and/or hydrocarbon fluids, such as extremely heavy crudes. The more polar of these solvents have also been found to be useful for extraction of salt and/or brine from core samples and to dewater heavy crude oils. These solvents (and especially the more polar solvents) may also be employed to clean core samples in preparation for performing various tests on the core sample. Further, the fact that these solvents have extremely low boiling points requires the use of a pressurized soxhlet in order to be able to perform the soxhlet extraction.

A simple experiment was performed, to verify that cyclopropane effectively extracts hydrocarbon fluids from a core sample without substantially affecting the petrophysical properties of the hydrocarbons. A core sample was saturated with a crude oil having known petrophysical properties before extraction with cyclopropane in a pressurized soxhlet assembly. The extracted core sample was then subjected to additional extraction with toluene by refluxing for 24 hours; the toluene exhibited no color after this 24 hour extraction demonstrating that the cyclopropane had already extracted the oil from the core. The measured API gravity of the original crude oil was 33.3 and the measured API gravity of the cyclopropane extracted crude oil was 32.7 Further, the original crude oil and the cyclopropane extracted crude oil were analyzed by gas chromatography. The resulting gas chromatographs are basically duplicates of each other, with the extracted crude oil chromatograph exhibiting a trace of solvent.

The use of near infrared techniques to characterize the API gravity of either the produced crude oil from the oil extracted by the above technique or the API gravity of the extract itself is also a portion of the present invention. More particularly, the spectra from these crude oil extracts may be employed to determine API gravity, density, or asphaltene content of the crude extract. Since near infrared spectroscopy is sensitive to subtle shifts in to C—H bonds, near infrared spectroscopy is particularly useful for characterizing hydrocarbons. However, the incomplete removal of the solvent for near infrared analysis does not significantly affect any results obtained, so long as the solvent has no C—H bonds or is present in a small quantity.

Further, a near infrared spectroscope may be employed to determine the API gravity of the actual crude oil, rather than extract which is found in the core sample. In particular, it has been found that some of the "light ends" of the crude oil may be washed away by the drilling fluids, or evaporate with time so that the API gravity of the crude oil from the formation may be slightly different from the API gravity of oil found in a core sample. However, the near infrared technique is amenable to determining either one or both of these API gravities.

In particular, the spectra of various crude oils having known API gravities have been analyzed by regression analysis to provide a correlation between the near infrared spectra of the extracts of the crude and the API gravity, density, or asphaltene content of these crudes. Thus, by employing the known coefficients from the correlations of these earlier known crudes and extracts, it is possible to determine the API gravity, density, or asphaltene content of an unknown crude from its extract. More specifically, near infrared measurements were made of produced crudes and their "topped" counterparts. The "topped" counterparts were created by heating the crude at 60° C. for 48 hours to simulate the loss of light ends from the coring process. The regression analysis was run on the near infrared spectra of the crudes and their topped counterparts, with each crude and its topped counterpart being assigned the same API gravity as the crude. The regression analysis was able to pick correlation wavelengths which are not very sensitive to the loss of light ends.

Good results have been found for using the "topped" counterpart as a predictor of the API gravity of the crude for medium to light crudes. However, for the heaviest crude the API gravity prediction from the topped counterpart is a few API degrees high. These results are presently believed to be caused by small bubbles of gaseous solvent in the crude or incomplete extraction by the solvent.

Extremely low gravity crudes may contain gas bubbles from the solvent used to extract the crude resulting in erroneous gravity and/or density determination. These bubbles may be removed by heating the crude slightly to allow the bubbles to escape or by using a lower boiling point solvent. In general, such bubbles cause the density to be lower than actual and the API gravity to be higher than normal.

Extremely low gravity, or heavy crudes may also contain significant amounts of water or brine that is very difficult to remove. Centrifuging such watered heavy crudes at high speeds for long times does not result in the removal of all of the water. However, the special solvent of the present invention may be employed to dewater such heavy crudes without significantly affecting the petrophysical properties of the crude oil. For such purposes, the ratio of the solvent volume to sample volume is preferably kept small to avoid any asphaltene precipitation.

In particular, twelve samples of crude oil had their density, API gravity, and asphaltene content determined by conventional methods. Each of the twelve samples also had its near infrared spectra measured and stored by a Technicon Infra-red Analyzer model 500. The analyzer was then programmed to determine the three best wavelengths and correlation coefficients that correlated the infrared spectra with the given densities, etc. using a linear regression algorithm provided with the analyzer. Although the analyzer was not told of the relationship relating API gravity and density, the analyzer surprisingly selected the same three wavelengths for gravity and density. Thus, near infrared spectra may be employed to determine density, API gravity, and asphaltene content.

Many other variations and modifications may be made in the techniques and apparatus hereinbefore described, by those having experience in this technology, without departing from the concepts of the present invention. Accordingly, it should be clearly understood that the method and apparatus depicted in the accompanying drawings and referred to in the foregoing description are illustrative only and are not intended as limitations on the scope of the present invention.

What is claimed is:

1. A method for determining the amount of fluids in a porous sample, comprising:
   providing a representative specimen of porous sample,
   extracting both aqueous and hydrocarbon fluids from said sample with a solvent capable of dissolving both aqueous and hydrocarbon fluids,
   separating said aqueous and hydrocarbon fluids, and
   determining the amount of aqueous and hydrocarbon fluid from said separated fluids.

2. A method as described in claim 1, wherein said solvent comprises,
   cyclopropane, vinyl chloride, freon R152A, or mixtures thereof.

3. A method as described in claim 1, wherein said porous sample is a sample containing heat sensitive material.

4. A method as described in claim 3, wherein said heat sensitive material comprises gypsum.

5. A method for determining at least one petrophysical property of a fluid in a porous sample, comprising:
   providing a representative specimen of porous sample,
   extracting both aqueous and hydrocarbon fluids from said sample with a solvent capable of dissolving both aqueous and hydrocarbon fluids,
   separating said squeous and hydrocarbon fluids, and
   determining said at least one petrophysical property of said fluid from said separated fluids.

6. A method as described in claim 5, wherein said petrophysical property is saturation of said fluid.

7. The method of claim 5, wherein said petrophysical property comprises API gravity, said fluid is crude oil and said determining step comprises determining the API gravity of the produced crude oil from the near infrared spectra of the extracted crude oil.

8. A method as described in claim 5, wherein said porous sample is a sample containing heat sensitive material.

9. A method for determining the pore volume of a porous sample containing aqueous and hydrocarbon fluids, comprising:

extracting said sample with a solvent capable of dissolving both aqueous and hydrocarbon fluids to remove said aqueous and hydrocarbon fluids from said sample, separating said solvent and aqueous fluids from said extracted hydrocarbon fluids by evaporation, condensing said aqueous fluids and said solvent separately from said hydrocarbon fluids, separating said aqueous fluids from said solvent, determining the volumes of said extracted hydrocarbon fluid and said separated aqueous fluid, and calculating said pore volume from said determined volumes.

* * * * *